(12) United States Patent
Rapier et al.

(10) Patent No.: US 11,058,470 B2
(45) Date of Patent: Jul. 13, 2021

(54) INSERTION TOOL FOR FLIP ANCHOR CABLE SYSTEM INSERTION

(71) Applicant: DEPUY SYNTHES PRODUCTS, INC., Raynham, MA (US)

(72) Inventors: Rhett A. Rapier, Trimbach (CH); Simon M. Bosshard, Bern (CH); This Aebi, Grenchen (CH); Darko Selkic, Gretchen (CH); Mario Wyss, Egerkingen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 329 days.

(21) Appl. No.: 16/262,079

(22) Filed: Jan. 30, 2019

(65) Prior Publication Data

US 2019/0159821 A1 May 30, 2019

Related U.S. Application Data

(63) Continuation of application No. 15/151,144, filed on May 10, 2016, now Pat. No. 10,238,444.

(51) Int. Cl.
*A61B 17/88* (2006.01)
*A61B 17/68* (2006.01)
*F16C 1/12* (2006.01)

(52) U.S. Cl.
CPC ........ *A61B 17/8861* (2013.01); *A61B 17/683* (2013.01); *A61B 17/685* (2013.01);
(Continued)

(58) Field of Classification Search
CPC ............ A61B 17/0401; A61B 17/0469; A61B 17/0482; A61B 17/0483; A61B 17/2909;
(Continued)

(56) References Cited

U.S. PATENT DOCUMENTS 5,814,051 A 9/1998 Wenstrom, Jr.
5,944,724 A 8/1999 Lizardi
(Continued)

FOREIGN PATENT DOCUMENTS

WO 97/25928 7/1997

OTHER PUBLICATIONS

"Notification of Transmittal of the International Search Report and Written Opinion", for PCT/US2017/031641 dated Aug. 3,2017.

*Primary Examiner* — Samuel S Hanna
(74) *Attorney, Agent, or Firm* — Kramer Amado PC

(57) ABSTRACT

An insertion tool for deploying a flip anchor cable, including: a mechanism having a safety button and a slider, wherein the mechanism is configured to apply a clamping force on a portion of the flip anchor cable when the mechanism is in a first position; an inner tube having a proximal end connected to the mechanism configured to house a second portion of the flip anchor cable; a handle including a safety button opening and a slider opening, wherein the handle is configured to enclose a portion of the mechanism; and an outer tube having a proximal end connected to the handle configured to receive the inner tube; wherein the mechanism is configured to decrease the clamping force on the flip anchor cable when the mechanism is in a second position and to deploy a flip anchor of the flip anchor cable in the second position.

8 Claims, 7 Drawing Sheets

(52) U.S. Cl.
CPC ............ *A61B 17/8872* (2013.01); *F16C 1/12* (2013.01); *A61B 2017/681* (2013.01)

(58) Field of Classification Search
CPC .......... A61B 2017/0409; A61B 17/683; A61B 17/8861; A61B 17/8872; A61B 2017/681; F16C 1/12
See application file for complete search history.

(56) References Cited

U.S. PATENT DOCUMENTS

| | | | |
|---|---|---|---|
| 6,068,648 A * | 5/2000 | Cole | .................... A61B 17/683 606/232 |
| 6,544,267 B1 | 4/2003 | Cole | |
| 6,761,722 B2 | 7/2004 | Cole | |
| 2002/0188301 A1 | 12/2002 | Dallara | |
| 2006/0229623 A1 | 10/2006 | Bonutti et al. | |
| 2012/0004665 A1 | 1/2012 | Defossez et al. | |

* cited by examiner

INSERTION TOOL FOR FLIP ANCHOR CABLE SYSTEM INSERTION

CROSS REFERENCE To RELATED APPLICATION

This application is a continuation of U.S. patent application Ser. No. 15/151,144, filed May 10, 2016, the entire disclosure of which is hereby incorporated by reference for all purposes as if fully set forth herein.

TECHNICAL FIELD

Various exemplary embodiments disclosed herein relate generally to an insertion tool for inserting a flip anchor cable.

BACKGROUND

It is a common requirement in orthopedic surgical procedures to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant the anchoring devices. The enlarged access site may increase patient pain and lengthen recovery time. Further, in some locations it is difficult and impractical to make large access points to reach the appropriate site because of surrounding joints and vessels. Even with devices that penetrate the tissue in a substantially linear manner, i.e., lag bolts, the fracture must often be reduced before drilling and insertion of the bolt. Further, some of these devices may be difficult to use since it may be hard to reduce a fracture between two bone segments and maintain that reduction while the device is inserted. This is particularly true with small bone fragments where the use of threaded implants may tend to rotate one bone segment with respect to another, thereby creating a misalignment between the fragments.

Cerclage systems provide an alternative to implants that must penetrate the bone to achieve fixation. These systems rely on passing a cable around two segments of bone and then tensioning the cable to squeeze the bone segments together. A significant drawback of these systems is that they require access around the entire bone.

A flip anchor cable system provides a convenient and effective system for securing two segments of tissue together. Such a system may be operable through a relatively small insertion opening or openings to securely hold two tissue segments.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a insertion tool for deploying a flip anchor cable, including: a mechanism having a safety button and a slider, wherein the mechanism is configured to apply a clamping force on a portion of the flip anchor cable when the mechanism is in a first position; an inner tube having a proximal end connected to the mechanism configured to house a second portion of the flip anchor cable; a handle including a safety button opening and a slider opening, wherein the handle is configured to enclose a portion of the mechanism; and an outer tube having a proximal end connected to the handle configured to receive the inner tube; wherein the mechanism is configured to decrease the clamping force on the flip anchor cable when the mechanism is in a second position and to deploy a flip anchor of the flip anchor cable in the second position.

Various embodiments are described wherein the mechanism further includes: a safety button protrusion; and a safety button retainer configured to engage the safety button protrusion when the safety button is depressed to fix the safety button in a depressed position.

Various embodiments are described wherein the safety button in the depressed position allows the mechanism to be placed in the second position by the application of a sliding force on the slider.

Various embodiments are described wherein the mechanism further includes; a cable retaining member; and a cable retaining protrusion connected to the cable retaining member, wherein the cable retaining protrusion is configured to apply the clamping force on the flip anchor cable in the first position.

Various embodiments are described wherein the handle further includes a cable retaining stop configured to engage the cable retaining member to apply the clamping force on the flip anchor cable in the first position.

Various embodiments are described wherein the cable retaining member is configured to engage the cable retaining stop in the second position to prevent the mechanism from returning to the first position.

Various embodiments are described wherein: the mechanism further includes: a cable retaining member; and a locking member connected to the cable retaining member; and the handle further includes a single-use stop configured to engage the locking member in the second position to prevent the mechanism from returning to the first position.

Various embodiments are described wherein the locking member is configured to produce a sound as it slides over the single-use stop when the mechanism slides from the first position to the second position when a sliding force is applied to the slider.

Various embodiments are described wherein the handle includes an orientation indicator on the exterior of the handle.

Various embodiments are described wherein the handle includes a plurality of cable stays configured to secure the flip anchor cable inside the handle.

Various embodiments are described wherein the handle includes a plurality of cable guides configured to facilitate unfolding of the flip anchor cable inside the handle.

Various embodiments are described wherein handle includes a cable rod support configured to secure the cable rod of the flip anchor cable inside the handle.

Various embodiments are described wherein a distal end of the outer tube is configured to receive a proximal end of the flip anchor to secure the flip anchor.

Various embodiments are described wherein the inner tube has a distal end configured to engage the proximal end of the flip anchor and configured to push the proximal end of the flip anchor out of the distal end of the outer tube when the mechanism slides from the first position to the second position when a sliding force is applied to the slider.

Various embodiments are described wherein the mechanism further includes: button support member connected to the safety button and the slider; a central support member flexibly connected to the button support member; and cable retaining member flexibly connected to the central support member.

Various embodiments are described wherein the mechanism further includes: a safety button protrusion; a safety button retainer connected to the central support member configured to engage the safety button protrusion when the safety button is depressed to fix the safety button in a depressed position; a cable retaining protrusion connected to the cable retaining member, wherein the cable retaining protrusion is configured to apply the clamping force on the flip anchor cable in the first position; and a locking member connected to the cable retaining member.

Various embodiments are described wherein the housing is configured to enclose a third portion of the cable and a cable rod attached to the third portion of the cable.

Further various embodiments relate to a insertion tool, including: a flip anchor cable including flip anchor, a cable rod, and a cable connected to the flip anchor at a distal end and connected to the cable rod at the proximal end; a mechanism having a safety button and a slider, wherein the mechanism is configured to apply a clamping force on a first portion of the flip anchor cable when the mechanism is in a first position; an inner tube having a proximal end connected to the mechanism configured to house a second portion of the flip anchor cable; a handle including a safety button opening and a slider opening, wherein the handle is configured to enclose a portion of the mechanism; and an outer tube having a proximal end connected to the handle configured to receive the inner tube; wherein the mechanism is configured to decrease the clamping force on the flip anchor cable when the mechanism is in a second position and to deploy a flip anchor of the flip anchor cable in the second position.

Various embodiments are described wherein the flip anchor includes a proximal end that is inside a distal end of the outer tube to secure the flip anchor.

Various embodiments are described wherein the flip anchor includes a shoulder adjacent the proximal end wherein the shoulder is configured to engage a distal end of the inner tube and wherein the distal end of the inner tube pushes the shoulder to move the flip anchor out of the distal end of the outer tube when the mechanism slides from the first position to the second position when a sliding force is applied to the slider.

Various embodiments are described wherein the flip anchor deploys by the proximal end of the flip anchor rotating away from the cable when the distal end of the inner tube pushes the shoulder to move the flip anchor out of the distal end.

Various embodiments are described wherein the housing is configured to enclose a third portion of the cable and the cable rod.

Further various embodiments relate to a mechanism for an insertion tool for deploying a flip anchor cable, improving: a safety button; a slider; a button support member connected to the safety button and the slider; a central support member flexibly connected to the button support member; and a cable retaining member flexibly connected to the central support member, wherein the cable retaining member is configured to apply a clamping force on a portion of the flip anchor cable when the mechanism is in a first position, and decrease the clamping force on the flip anchor cable when the mechanism is in a second position.

Various embodiments are described further including: a safety button protrusion; and a safety button retainer configured to engage the safety button protrusion when the safety button is depressed to fix the safety button in a depressed position.

Various embodiments are described wherein the safety button in the depressed position allows the mechanism to be placed in the second position by the application of a sliding force on the slider.

Various embodiments are described wherein the cable retaining member further includes a cable retaining protrusion connected to the cable retaining member, wherein the cable retaining protrusion is configured to apply the clamping force on the flip anchor cable in the first position.

Various embodiments are described wherein the mechanism further includes a locking member connected to the cable retaining member configured to engage a single-use stop on a handle of the insertion tool, wherein the locking member is configured to engage the single-use stop in the second position to prevent the mechanism from returning to the first position.

Is contemplated that various combinations of the embodiments described herein may be made resulting in additional embodiments that are within the scope of the invention described herein.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1A:
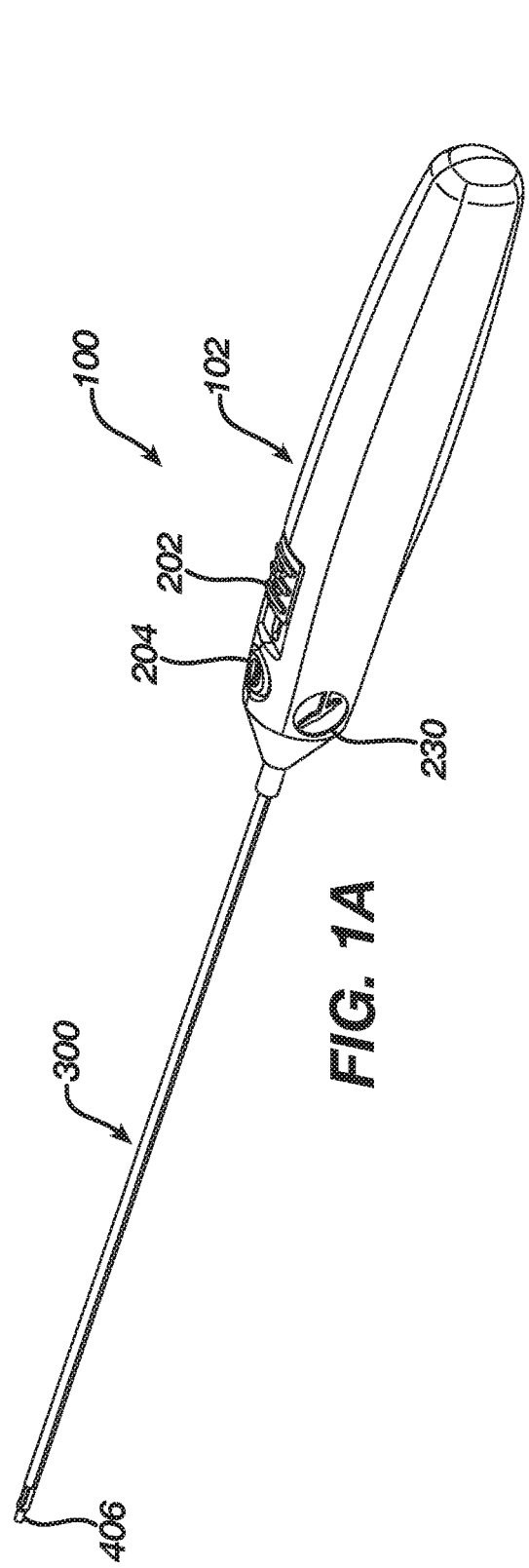
FIGS. 1A, 1B, and 1C provide perspective, side, and top views of the insertion tool, respectively.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiment A flip anchor cable is described in U.S. Pat. No. 6,761,722 to Cole et al. ("Cole"), which is hereby incorporated by reference for all purposes as if fully set forth herein. The flip anchor cable may be used to anchor tissue, for example, bone, cartilage, ligaments, tendons, muscle, etc. For example, the flip anchor cable may be used to reduce and secure a bone fracture. A hole may be drilled through the bone and the cable inserted through the hole. The flip anchor cable has an anchor at the end of the cable that is aligned with the cable during insertion. Once the anchor passes through the bone, the anchor rotates so that as the cable is then pulled back through the insertion hole, and the anchor is affixed to the bone surrounding the insertion hole. As tension is applied to the cable, the fracture in the bone may be reduced and secured. The cable may then be fixed in place by placing a ferrule over the cable and crimping the ferrule in place to securely anchor the reduced fracture. Other methods of securing the cable are also discussed in Cole.

Embodiments of an insertion tool that facilitate the insertion of the flip anchor cable are described below. This insertion tool provides the following features that facilitate the insertion of the flip anchor cable.

The insertion tool provides faster insertion of the flip anchor cable resulting in a shorter insertion time. The insertion tool also provides easier handling of the flip anchor cable to reduce the attention that a user has to give to handling the insertion of the flip anchor cable. Further, the insertion tool facilitates one handed use which allows the user to use their other hand for other tasks. The insertion tool protects and covers the cable which allows the cable to remain sterile and also makes handling the flip anchor cable simpler. Also, the insertion tool may be a single use tool meaning that there is no reprocessing time and cost. Further, the insertion tool provides a ready to use insertion system that does not require any assembly. This allows the user to immediately insert the flip anchor cable after removal from the packaging. As the insertion tool is pre-assembled and pre-positioned, the user may directly insert the flip anchor cable system directly after boring a hole.

Figure 1B:
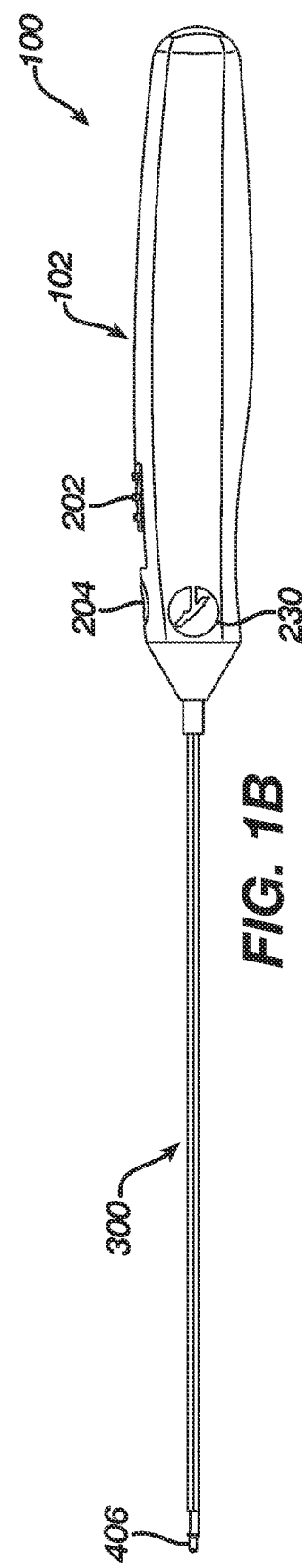
Figure 1C:
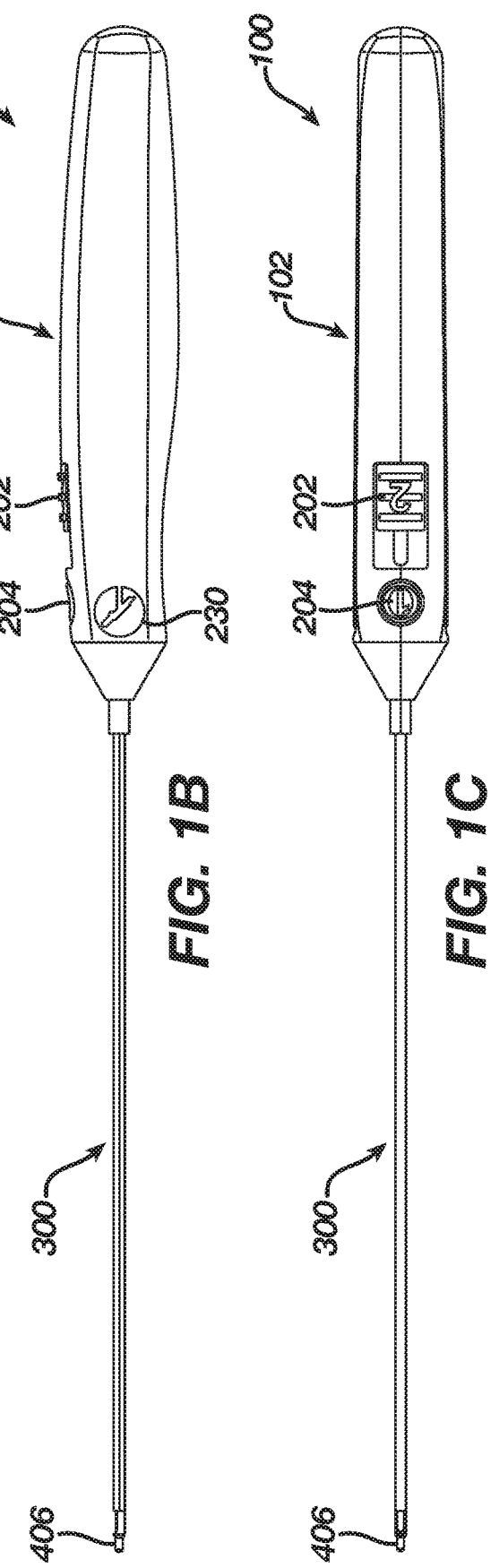

FIGS. 1A, 1B, and 1C provide perspective, side, and top views of the insertion tool, respectively. The insertion tool 100 include a handle 102 and an outer tube 300 connected to the handle 102. A flip anchor 406 that is part of a flip anchor cable protrudes from the outer tube 300. The cable that is part of the flip anchor cable extends through the outer tube 300 into the handle 102 where the cable is stored in the handle as will be shown below.

The handle 102 also includes a slider 202 and a safety button 204. As will be described further below, the safety button 204 may be pressed and then the slider 202 may be pushed forward towards the outer tube 300. This pushes the flip anchor 406 forward and free from the outer tube 300 to allow for the flip anchor cable to be deployed. The handle 102 also includes an orientation indicator 230 that shows the orientation of the flip anchor 406 as it deploys. This will assist the user in orienting the insertion tool 100 so that the flip anchor 406 will deploy in a chosen orientation. The orientation indicator 230 also allows for proper orientation of the flip anchor 406 when the user is unable to see the end of the insertion tool.

Figure 2:
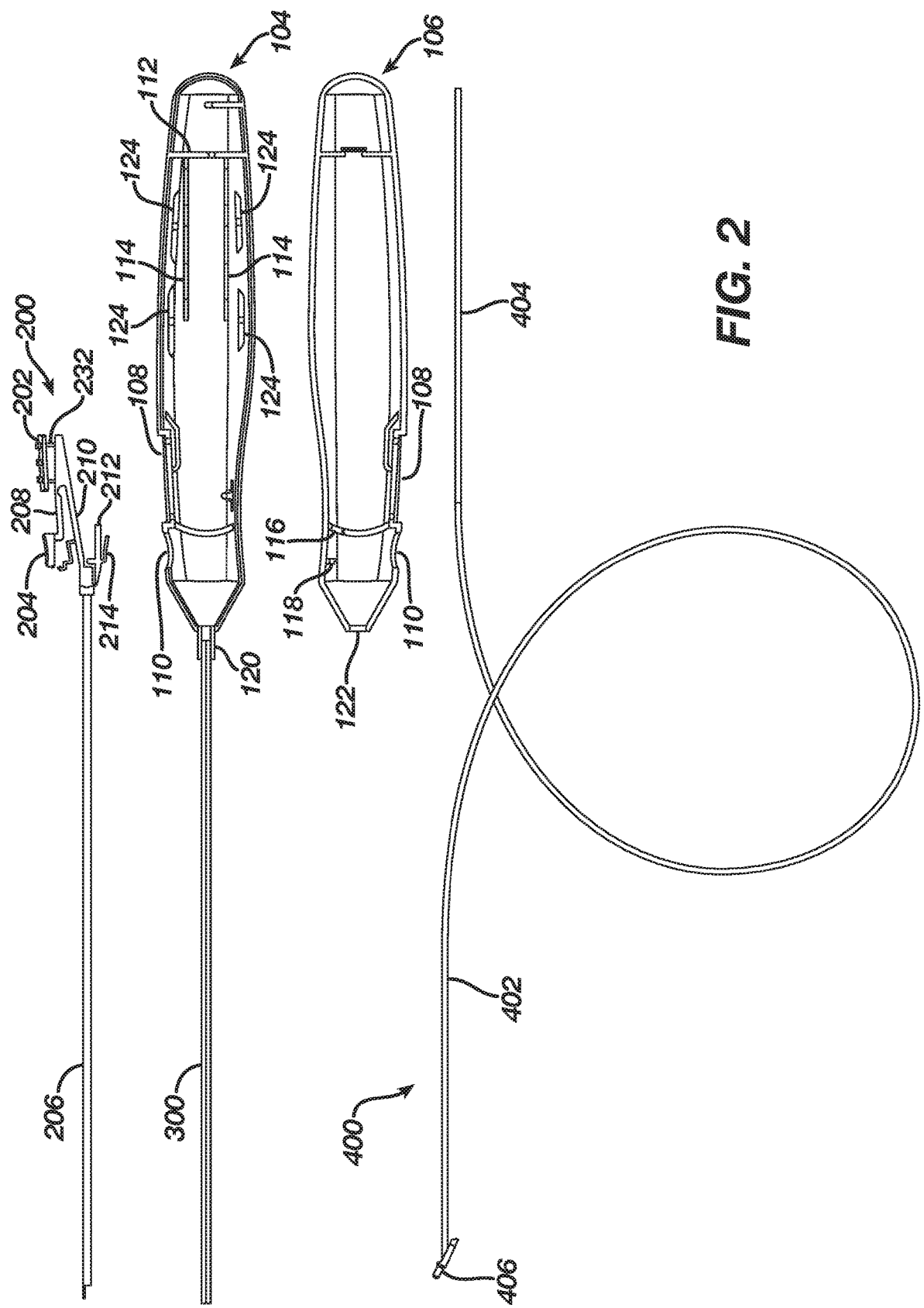
FIG. 2 illustrates an expanded view of the insertion tool.

FIG. 2 illustrates an expanded view of the insertion tool 100. The insertion tool 100 includes a first handle portion 104, a second handle portion 106, a mechanism 200, an inner tube 206, the outer tube 300, and a flip anchor cable 400.

FIGS. 5A-5D show side and perspective views of the first handle portion and the second handle portion, respectively. As shown in FIGS. 2 and 5A-5D, the first handle portion 104 includes a cylindrical mount 120 at a distal end of the first handle portion 104. The cylindrical mount 120 accepts a proximal end of the outer tube 300 so as to mount the outer tube 300 to the first handle portion 104. The second handle portion 106 includes a mating opening 122 that mates with the cylindrical mount 120.

The first handle portion 104 and the second handle portion 106 also include a safety button opening 110. The two safety button openings 110 combine to form a single opening in the handle 102 that corresponds to the safety button 204. The shape of the safety button opening 110 and the safety button 204 complement one another so that the safety button 204 fits in the safety button opening and is exposed to the user. Also, when the safety button 204 is exposed to the user, it prevents the mechanism 200 from sliding as will be discussed in further detail below.

The first handle portion 104 and the second handle portion 106 also include a slider opening 108. The two slider openings 108 combine to form a single opening that corresponds to the slider 202. This combined slider opening is generally slot shaped and may accommodate a slider support 232 (see FIG. 2 and FIG. 4B) that fits in the combined slider opening to allow the slider to move along the combined slider opening. The slider opening 108 may take any shape that accommodated the sliding of the slider 202 and the slider support 232.

The first handle portion 104 may also include a cable rod support 112. The cable rod support 112 may extend as shown between two sides of the first handle portion 104. The cable rod support 112 may include a slot 126 that accepts and secures the cable rod 404 in the first handle portion 104.

The first handle portion 104 may include cable stays 124. The cable stays accept and secure a portion of the cable 402 when the cable 402 is folded and stored inside the handle 102. Further, the first handle portion 104 may include cable guides 114. The cable guides are shown as having a wave shape that facilitates the unfolding of the cable 402 when the cable is deployed and pulled out of the insertion tool 100. When the cable 402 is folded in the handle 102, the cable 402 may cross the handle across the lower portions of the cable guides 114. As the cable is pulled out it will move up the wave shape to allow for smoother deployment of the cable 402 from the insertion tool 100. The cable guides also reduce the amount of force needed to pull the cable 402 out of the cable stays 124 and out of the insertion tool 100.

The second handle portion 106 may include a cable retaining stop 116. The cable retaining stop 116 applies a force to a cable retaining member 212 of the mechanism 200. While the cable retaining stop 116 is shown as being part of the second handle portion 106, it may be instead a part of the first handle portion 104. Further, the cable retaining stop 116 may also be a part of both the first handle portion 104 and the second handle portion 106 that combine to apply the force to the cable retaining member 212.

The second handle portion 106 may include a single-use stop 118. The single-use stop 118 interacts with a locking member 214 of the mechanism 200. As will be described in further detail below, the single-use stop 118 may prevent the mechanism 200 from sliding backwards after the slider 202 has been pushed forward by a user. While the single-use stop 118 is shown as being part of the second handle portion 106, it may be instead a part of the first handle portion 104. Further, the single-use stop 118 may also be a part of both the first handle portion 104 and the second handle portion 106 that combine to prevent the mechanism 200 from sliding backwards.

Figure 4A:
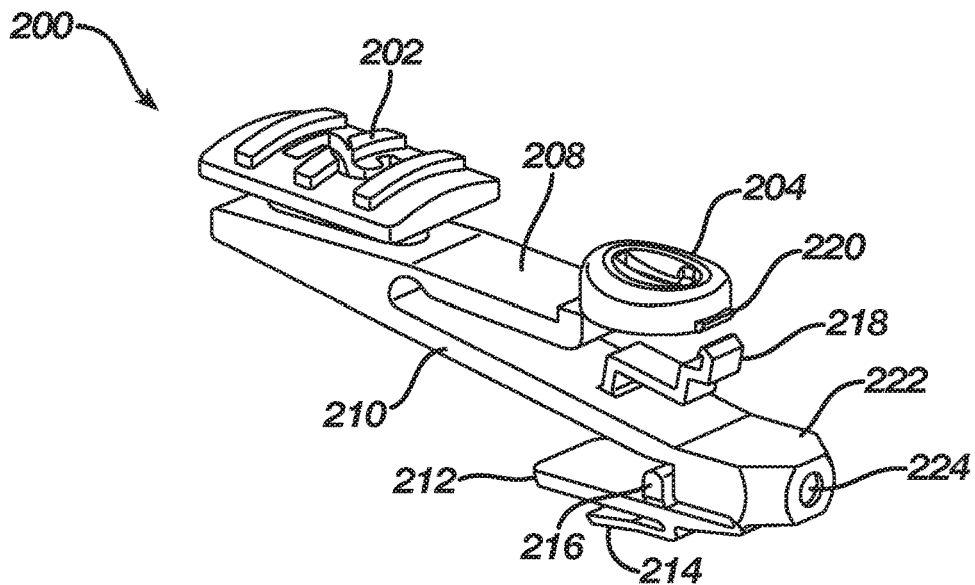
FIGS. 4A-4C show perspective, side, and top views of the mechanism, respectively.
Figure 4B:
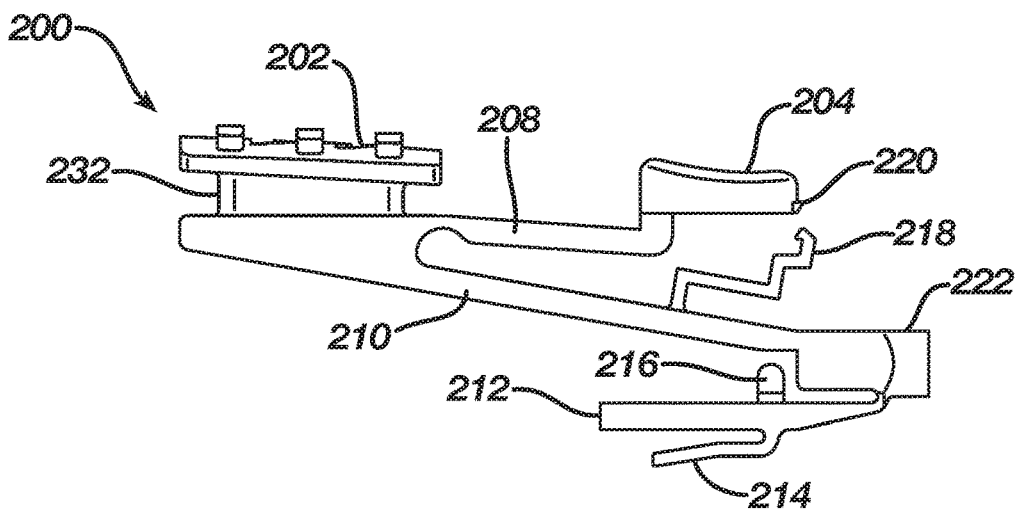
Figure 4C:
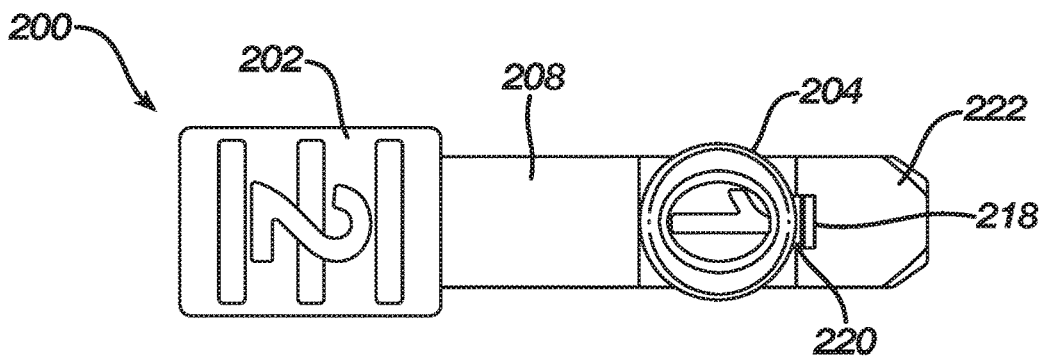
Figure 5A:
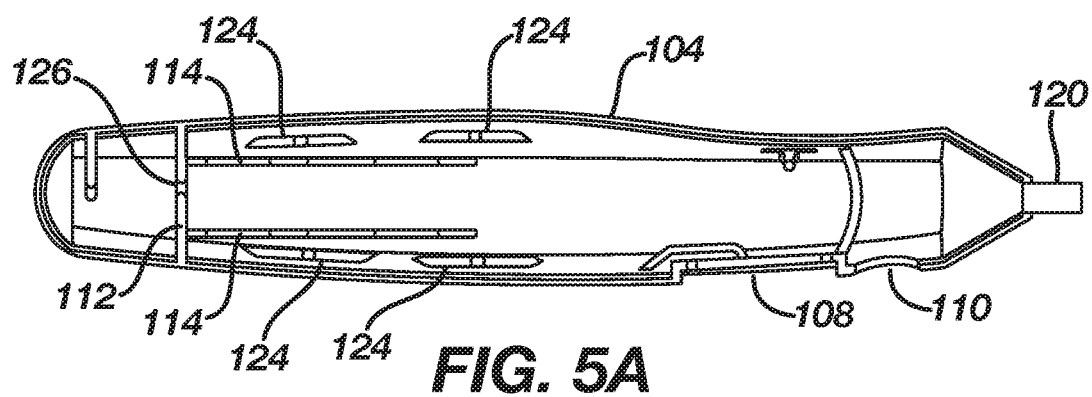
FIGS. 5A-5D show side and perspective views of the first handle portion and the second handle portion, respectively.
Figure 5B:
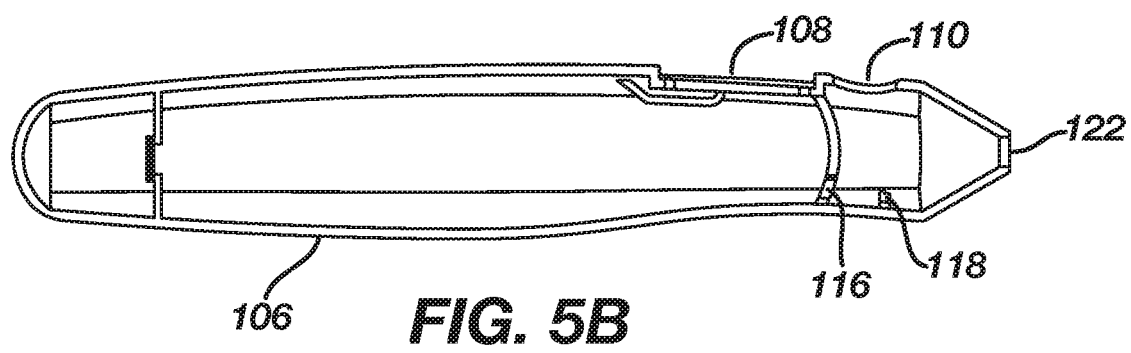
Figure 5C:
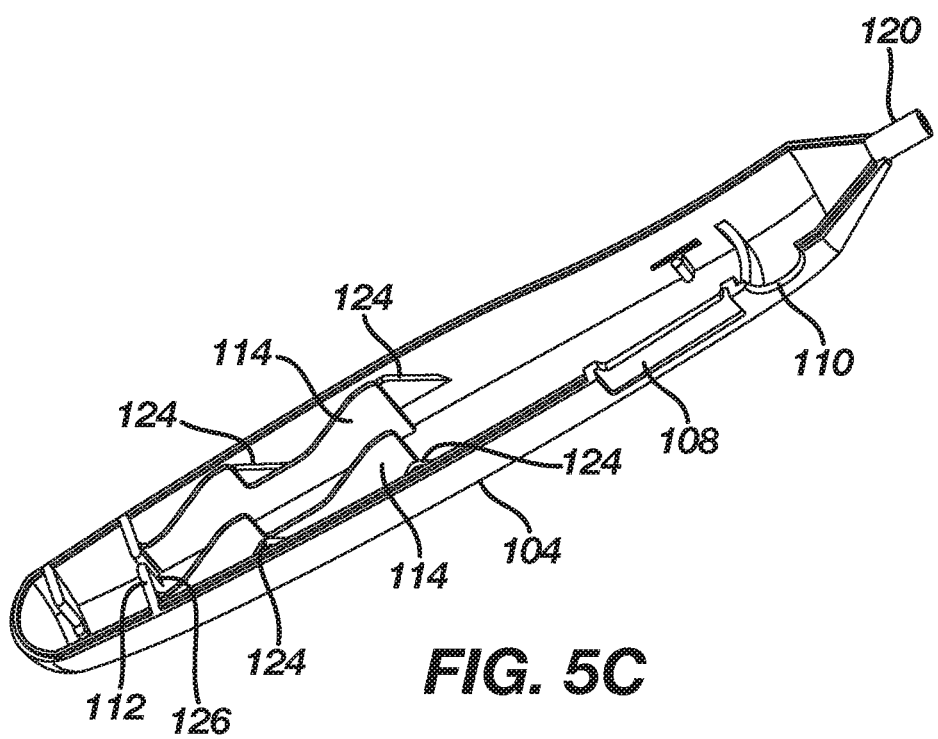
Figure 5D:
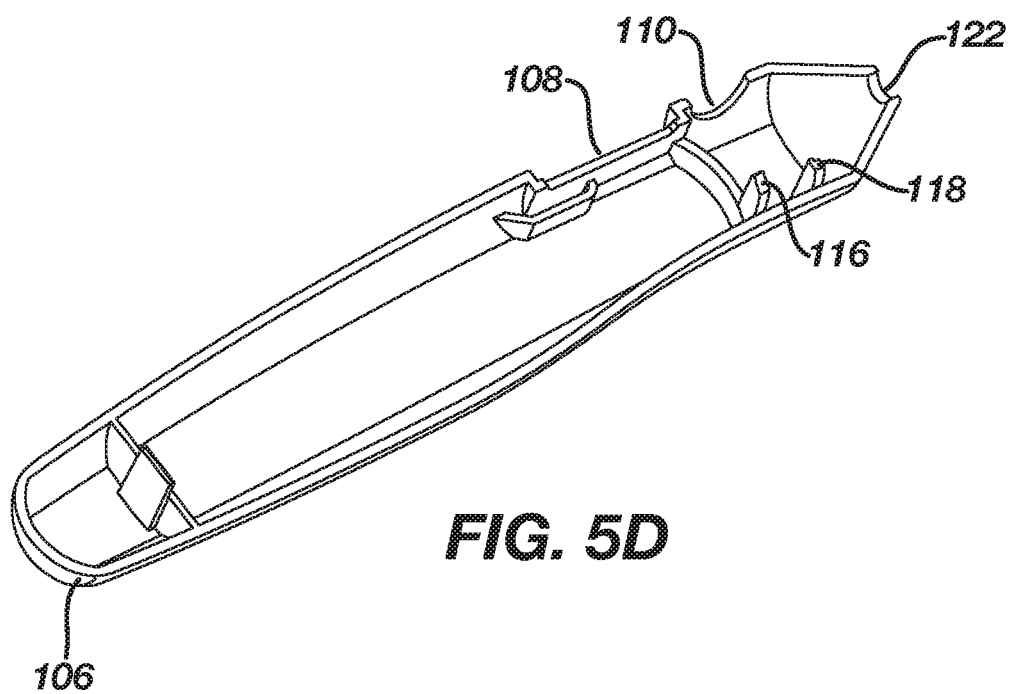

FIGS. 4A-4C show perspective, side, and top views of the mechanism, respectively. As shown in FIGS. 2 and 4A-4C, an inner tube 206 is attached at a proximal end to the mechanism 200. The flip anchor cable 400 is inserted into the inner tube 206 and passes through the inner tube 206 as the flip anchor cable 400 is deployed. Further, the inner tube 206 fits and slides within the outer tube 300. The mechanism may include an end portion 222 having an end hole 224. The end hole 224 accepts the proximal end of the inner tube 206 to attach the inner tube 206 to the mechanism 200. Further, the end hole 224 extends through the end portion 222 so that the flip anchor cable 400 can pass through the end hole 224 to interact with other parts of the mechanism.

The mechanism 200 may include a button support member 208. The safety button 204 may be connected to the button support member 208. Also, the slider 202 may be connected to the button support member 208 via a slider support 232. In other embodiments of the mechanism, the slider may be directly connected to the button support member 208 without a slider support 232.

The safety button 204 may also include a safety button protrusion 220. The safety button protrusion 220 may engage a safety button retainer 218 as will be described further below. In other embodiments, the safety button protrusion 220 may instead extend from the button support member 208.

The mechanism 200 also may include a central support member 210. The central support member 210 may connect with the button support member 208 at one end and with the end portion 222 at the other end. The connection between the central support member 210 and the button support member 208 may be flexible to allow the central support member 210 and the button support member 208 to move relative to one another when forces are applied to the mechanism 200.

The safety button retainer 218 may also be attached to the central support member 210. When the safety button 204 is depressed by the user, the button support member 208 flexes towards the central support member 210, thus bringing the safety button protrusion 220 into engagement with the safety button retainer 218. The engagement between the safety button protrusion 220 and the safety button retainer 218 fixes the safety button 204 in place, i.e., in a depressed position, to prevent the button support member 208 from springing back away from the central support member 210. While shapes are shown for the safety button retainer 218 and the safety button protrusion 220, other shapes may be used that facilitate locking the safety button 204 after it has been depressed.

The mechanism 200 may also include a cable retaining member 212 that is flexibly connected to the end portion 222. In other embodiments, the cable retaining member 212 may also be connected to the central support member 210. The cable retaining member 212 may have a cable retaining protrusion 216 that extends towards the central support member 210. The cable retaining protrusion 216 may be near where the cable 402 extends out from the end hole 224 so as to engage and clamp a portion of the cable 402. The cable retaining member 212 may also be connected to a locking member 214. The locking member 214 extends away from the cable retaining member 212 and may move relative to the cable retaining member 212 when a force is applied. The operation of the cable retaining member 212, the cable retaining protrusion 216, and the locking member 214 will be described further below. In various embodiments, the shapes and locations of the cable retaining member 212, the cable retaining protrusion 216, and the locking member 214 may vary as long as they provide the functionality that will be described further below.

In FIG. 4C, the safety button 204 is shown as having a numeral "1" on its surface. Likewise, the slider 202 is shown as having a number "2" on its surface. This is to help guide the user in the operation of the insertion tool where the safety button 204 is first depressed, and then the slider 202 may be slid forward to begin deployment of the flip anchor cable 400.

FIG. 2 also shows the flip anchor cable 400 outside of the insertion tool. The flip anchor cable 400 may include the flip anchor 406 attached to distal end of the cable 402. The cable rod 404 be connected to proximal end of the cable 402. The flip anchor 406 may be attached to the cable in a flexible manner, where the flip anchor may rotate relative to the cable. In one position, the flip anchor 406 may be aligned with the cable 402 and held in place for example by the outer tube 300. The flip anchor 406 may be connected to the cable 402 so that it is naturally at an angle to the cable 402, so that when the flip anchor 406 is free of the outer tube 300, it will rotate away from the cable 402 so that it may be deployed.

The mechanism 200 may be made as a single unit out of a single material. The material may have the needed strength and flexibility to accomplish the described functionality. The mechanism 200 may be made using low cost materials and manufacturing processes. This allows for a single use insertion tool 100, while keeping the cost of the flip anchor cable system down.

Figure 3:
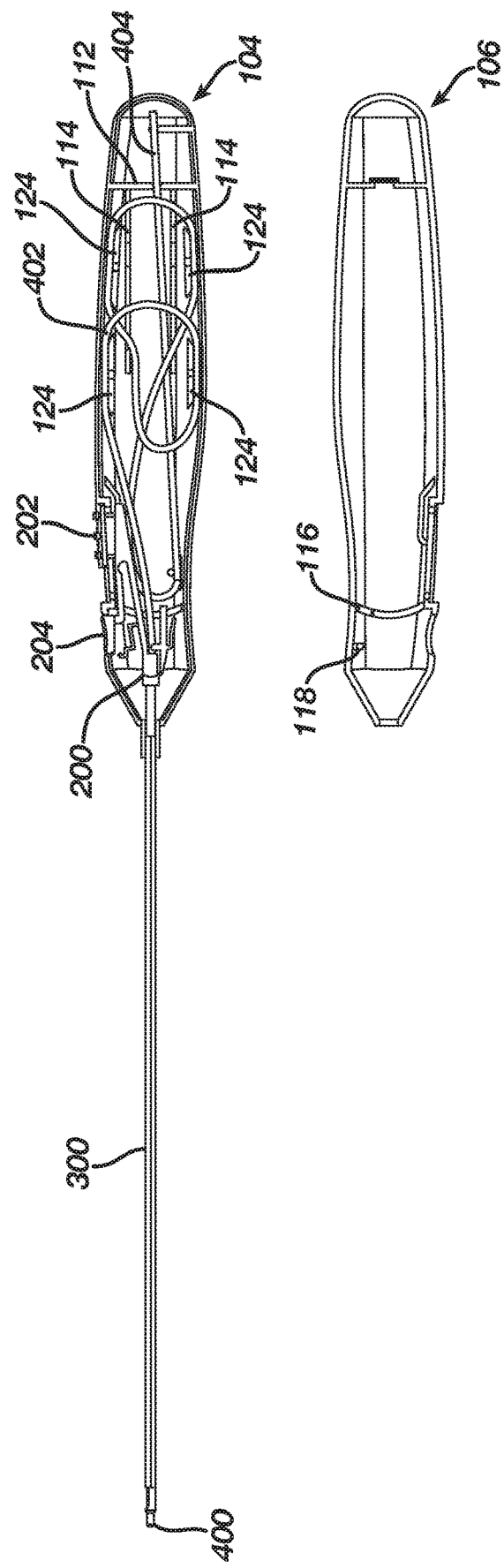
FIG. 3 illustrates the assembled insertion tool with the second handle member removed to show the interior of the assembled insertion tool.

FIG. 3 illustrates the assembled insertion tool with the second handle member removed to show the interior of the assembled insertion tool. The mechanism 200 along with the inner tube 206 are installed so that the inner tube 206 is inside the outer tube 300 and the safety button 204 is in the opening 110 (not shown in FIG. 3.) The flip anchor cable 400 is also installed. The cable rod 404 rests in the cable rod support 112. A portion of the cable 402 extends from the cable rod 404 and then enters the end hole 224 (not shown in FIG. 3). This portion of the cable 402 is folded as shown and held in place by the cable stays 124. This portion of the cable may be folded to cross a lower portion of the cable guides 114. Another portion of the cable 402 then further extends through the inner tube 206 so that the flip anchor 406 is fixed in the end of the outer tube 300.

The cable retaining member 212 is biased upward by the cable retaining stop 116 so that the cable retaining protrusion 216 is in contact with the cable 402, thereby clamping the cable 402 in place. This clamping fixes the cable 402 in place to keep the flip anchor 406 in place and to prevent the cable from being inadvertently pulled out of the insertion tool 100.

Figure 6:
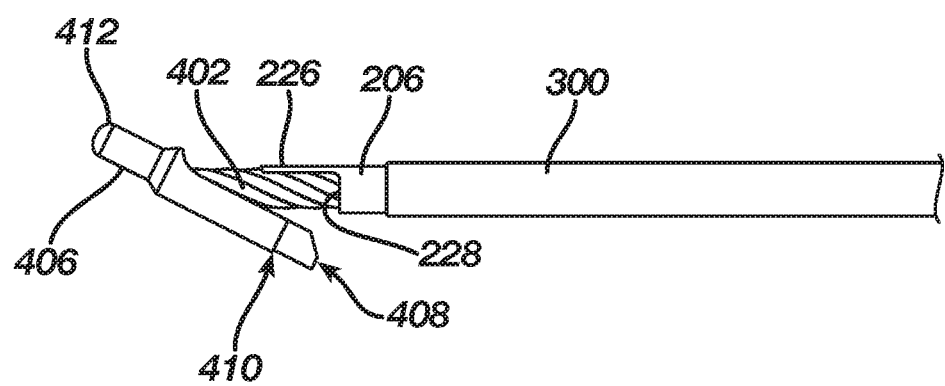
FIG. 6 illustrates the flip anchor at the end of the flip anchor cable extending from the inner tube and the outer tube.

FIG. 6 illustrates the flip anchor at the end of the flip anchor cable extending from the inner tube and the outer tube. The flip anchor 406 may have a proximal end 408 and a distal end 412. The flip anchor 406 may be fixed to the distal end of the cable 402, and the flip anchor 406 may be able to rotate away from the cable 402. The proximal end 408 of the flip anchor 406 may have a shape that is complementary to shape of the end of the inner tube 206. For example, the inner tube 206 may have an inner tube end member 226 that extends from inner tube 206. This inner tube end member 226 extends along a portion of the cable 402 opposite the proximal end 408 of the flip anchor 406. Further, at the end of the inner tube 206 is an inner tube pushing surface 228 that complements the proximal end 408 of the flip anchor 406. When a user pushes the slider 202 (not shown) forward, the inner tube pushing surface 228 pushes the flip anchor 406 forward and free of the outer tube 300 so that the flip anchor 406 may deploy.

The flip anchor 406 may also include a shoulder 410 adjacent to the proximal end 408. The proximal end 408 may have a similar diameter as the inner tube 206 so that the proximal end 408 may be locked inside the end of the outer tube 300. The shoulder has a larger diameter than the proximal end 408 and as a result mates with the end of the outer tube 300.

The operation of the insertion tool 100 will now be described. After a user drills a hole in, for example, a bone, the end of the insertion tool 100 is placed in the hole until the distal end of the insertion tool passes completely through the hole in the bone. The insertion tool 100 may be rotated to a specific angular position about its long axis so that the flip anchor 406 has a desired position. The orientation marker 230 on the handle 102 helps guide this alignment.

The safety button 204 resides in the safety button opening 110 and this prevents the mechanism 200 from moving forward. Next, the user depresses the safety button 204 causing the safety button protrusion 220 to engage the safety button retainer 218. This fixes the safety button 204 in a depressed position, and the safety button 204 disengages the safety button opening. Now the user may apply a forward force on the slider 202 to slide the mechanism 200 forward.

Sliding the mechanism 200 forward has a number of different effects. First, as the cable retaining member 212 moves forward, it disengages from the cable retaining stop 116. This results in the cable retaining protrusion 216 decreasing its clamping force on the cable 402, which allows the flip anchor cable 400 to be pulled out of the insertion tool 100.

Second, as the locking member 214 moves forward, it passes over the single-use stop 118 and flexes downward. This may cause a snapping sound that provides an indication that the flip anchor 406 has been deployed. Further once the locking member 214 moves downward and over the single-use stop 118, the single-use stop 118 now blocks the locking member 214 from moving backward. This prevents the mechanism 200 from moving backward providing a single-use safety feature for the insertion tool 100.

In an alternative embodiment, the mechanism 200 may not have a locking member 214, and once the cable retaining member 212 moves downward and disengages from the cable retaining stop 116, the cable retaining stop 116 may now block the cable retaining member 212 from moving backward. This prevents the mechanism 200 from moving backward providing a single-use safety feature for the insertion tool 100.

Third, as the mechanism 200 moves forward the inner tube 206 moves forward pushing the proximal end 408 of the flip anchor 406 out of the end of the outer tube 300. This unlocks the flip anchor 406. The flip anchor 406 then rotates so that it may engage the bone around the hole.

The user may then pull the insertion tool 100 backwards to pull the cable 402 and the cable rod 404 out of the insertion tool. The cables guide 114 facilitates the unfolding of the cable 402 as the cable 402 is pulled out of the insertion tool 100.

Once the flip anchor cable 400 is completely pulled out of the insertion tool 100, the insertion tool 100 may be disposed of. Now the user may further manipulate and secure the cable as is known in the art.

The mechanism 200 and the insertion tool 100 allows for one time pressing of the safety button 204, which gives the user clear feedback on the status of the insertion tool 100. The safety button 204 and the slider 202 are close together on the top of the insertion tool 100 allowing for ease-of-use for both left and right handed users.

The mechanism 200 provides for safe operation of the insertion tool 100. As long as the safety button 204 is not pressed, the cable 402 is held by the mechanism 200 with a high clamping force between the cable 402 and the cable retaining protrusion 216. After pressing the safety button 204 and sliding the sliding button 202 in distal direction, the clamping force on the cable 402 decreases. Further, after the safety button 204 is pressed and the mechanism 200 is slid forward, the mechanism 200 has features that prevents the mechanism 200 from sliding backwards.

The design of the insertion system 100 facilitates operation using one hand. Other systems require multiple hands to correctly operate. This may be problematic as users are often required to use multiple instruments at one time. The insertion tool described herein allows the user to successfully insert the flip anchor cable, unlock the mechanism, release the cable, and remove the insertion tool with one hand.

As the insertion tool is preassembled and internally stores the cable, contamination or mishandling of the cable may be prevented. This means that the user has no direct contact with the cable until after it is inserted within the bone and the flip anchor is released. This minimizes risk, shortens the operating time, and decreases the potential for user error.

It should be appreciated by those skilled in the art that any diagrams or schematic drawings herein represent conceptual views of illustrative structures embodying the principles of the invention.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Further, various elements from the various embodiments may be combined to form other embodiments that are within the spirit and scope of the invention. Accordingly, the foregoing disclosure, description, and figures are for illustrative purposes only and do not in any way limit the invention, which is defined only by the claims.

What is claimed is:

1. An insertion tool, comprising:
   a flip anchor cable including a flip anchor, a cable rod, and a cable connected to the flip anchor at a distal end and connected to the cable rod at the proximal end;
   a mechanism having a safety button and a slider, wherein the mechanism is configured to apply a clamping force on a first portion of the flip anchor cable when the mechanism is in a first position;
   the mechanism further comprises a button support member connected to the safety button and the slider, a central support member flexibly connected to the button support member, a cable retaining member flexibly connected to the central support member, and a locking member connected to the cable retaining member configured to engage a single-use stop on the handle of the insertion tool, wherein the locking member is configured to engage the single-use stop in the position to prevent the mechanism from returning to the first position;

an inner tube having a proximal end connected to the mechanism configured to house a second portion of the flip anchor cable;

a handle including a safety button opening and a slider opening, wherein the handle is configured to enclose a portion of the mechanism, the safety button is engageable with the safety button opening to prevent movement of the mechanism relative to the handle, and the slider is configured to slide the mechanism along the slider elongated opening upon pressing the safety button to disengage the safety button opening; and an outer tube having a proximal end connected to the handle configured to receive the inner tube;

wherein the mechanism is configured to decrease the clamping force on the flip anchor cable when the mechanism is in a second position and to deploy the flip anchor of the flip anchor cable in the second position.

2. The insertion tool of claim 1, wherein the flip anchor includes a proximal end that is inside a distal end of the outer tube to secure the flip anchor.

3. The insertion tool of claim 2, wherein the flip anchor includes a shoulder adjacent the proximal end wherein the shoulder is configured to engage a distal end of the inner tube and wherein the distal end of the inner tube pushes the shoulder to move the flip anchor out of the distal end of the outer tube when the mechanism slides from the first position to the second position when a sliding force is applied to the slider.

4. The insertion tool of claim 3, wherein the flip anchor deploys by the proximal end of the flip anchor rotating away from the cable when the distal end of the inner tube pushes the shoulder to move the flip anchor out of the distal end.

5. The insertion tool of claim 1, wherein the housing is configured to enclose a third portion of the cable and the cable rod.

6. The insertion tool of claim 1, wherein the mechanism further comprises
a safety button protrusion; and
a safety button retainer configured to engage the safety button protrusion when the safety button is depressed to fix the safety button in a depressed position.

7. The insertion tool of claim 6, wherein the safety button in the depressed position allows the mechanism to be placed in the second position by the application of a sliding force on the slider.

8. The insertion tool of claim 1, wherein the cable retaining member further comprises a cable retaining protrusion connected to the cable retaining member, wherein the cable retaining protrusion is configured to apply the clamping force on the flip anchor cable in the first position.

* * * * *